US012629055B1

(12) United States Patent
Culbertson, II et al.

(10) Patent No.: US 12,629,055 B1
(45) Date of Patent: May 19, 2026

(54) SYSTEMS AND METHODS FOR TRACKING PHYSICAL WORK ACTIVITY

(71) Applicant: United Services Automobile Association (USAA), San Antonio, TX (US)

(72) Inventors: William Preston Culbertson, II, Plant City, FL (US); Gregory David Hansen, San Antonio, TX (US); Mark Anthony Lopez, Helotes, TX (US); Will Kerns Maney, San Antonio, TX (US); Keegan Patrick Hayes, San Antonio, TX (US); Steven Michael Bernstein, San Antonio, TX (US)

(73) Assignee: United Services Automobile Association (USAA), San Antonio, TX (US)

( * ) Notice: Subject to any disclaimer, the term of this patent is extended or adjusted under 35 U.S.C. 154(b) by 826 days.

(21) Appl. No.: 17/462,668

(22) Filed: Aug. 31, 2021

(51) Int. Cl.
*A61B 5/11* (2006.01)
*A61B 5/00* (2006.01)
*H02J 50/05* (2016.01)

(52) U.S. Cl.
CPC .......... *A61B 5/1118* (2013.01); *A61B 5/6803* (2013.01); *A61B 5/6804* (2013.01); *A61B 5/742* (2013.01); *H02J 50/05* (2016.02)

(58) Field of Classification Search
CPC ... A61B 5/1118; A61B 5/6803; A61B 5/6804; A61B 5/742; H02J 50/05
See application file for complete search history.

(56) References Cited

U.S. PATENT DOCUMENTS

| | | | | |
|---|---|---|---|---|
| 2014/0176422 | A1* | 6/2014 | Brumback | G06F 1/3265 |
| | | | | 345/156 |
| 2015/0084584 | A1* | 3/2015 | Monks | H02J 50/80 |
| | | | | 320/108 |
| 2016/0088090 | A1* | 3/2016 | Durham | H04L 67/125 |
| | | | | 709/201 |
| 2017/0055918 | A1* | 3/2017 | Hughes | A61B 5/7278 |
| 2017/0136296 | A1* | 5/2017 | Barrera | G16H 20/30 |
| 2017/0277138 | A1* | 9/2017 | Kaji | G06F 3/03547 |
| 2017/0344919 | A1* | 11/2017 | Chang | G09B 5/02 |
| 2019/0122036 | A1* | 4/2019 | Ward | G06Q 10/06393 |
| 2019/0295025 | A1* | 9/2019 | Hyodo | G06F 3/011 |

(Continued)

FOREIGN PATENT DOCUMENTS

WO      WO-2020008162 A1 *   1/2020   .............. H05B 3/12

OTHER PUBLICATIONS

Wang (CN 204540929) English Translation (Year: 2015).*

*Primary Examiner* — Michael J Dalbo
(74) *Attorney, Agent, or Firm* — Fletcher Yoder, P.C.

(57) ABSTRACT

Embodiments of the present disclosure include systems and methods for tracking physical work activity by, for example, embedding sensors in items of work clothing. The physical activity data that is tracked by the sensors may be correlated with and compared to known physical activity data to determine the type of work function that corresponds to the physical activity data. Based on this, actual performance of the work function may be compared to the idealized version of the work function to, for example, grade the performance of the work function, identify specific deficiencies in the performance of the work function, recommend modifications to performance of the work function, and so forth.

15 Claims, 8 Drawing Sheets

(56) References Cited

U.S. PATENT DOCUMENTS

| | | | |
|---|---|---|---|
| 2020/0312453 A1* | 10/2020 | Raisanen | G06F 3/016 |
| 2021/0026440 A1* | 1/2021 | Poupyrev | A61B 5/1118 |
| 2021/0031112 A1* | 2/2021 | Dugan | A61B 5/681 |
| 2021/0186432 A1* | 6/2021 | Kodama | A61B 5/7275 |
| 2022/0005580 A1* | 1/2022 | Pavlov | A61B 5/486 |
| 2022/0108325 A1* | 4/2022 | Trunck | G06Q 10/083 |
| 2022/0210628 A1* | 6/2022 | Ka Dlamini | A61B 5/6804 |
| 2022/0277254 A1* | 9/2022 | Feeney | G08B 21/02 |
| 2023/0005595 A1* | 1/2023 | Garriga Calleja | A61B 5/6898 |

* cited by examiner

POOR
(SCORE = 50)

126

HEAD NOT
STRAIGHT

KNEES
NOT BENT

PERFECT
(SCORE = 100)

128

HEAD
STRAIGHT

KNEES
BENT

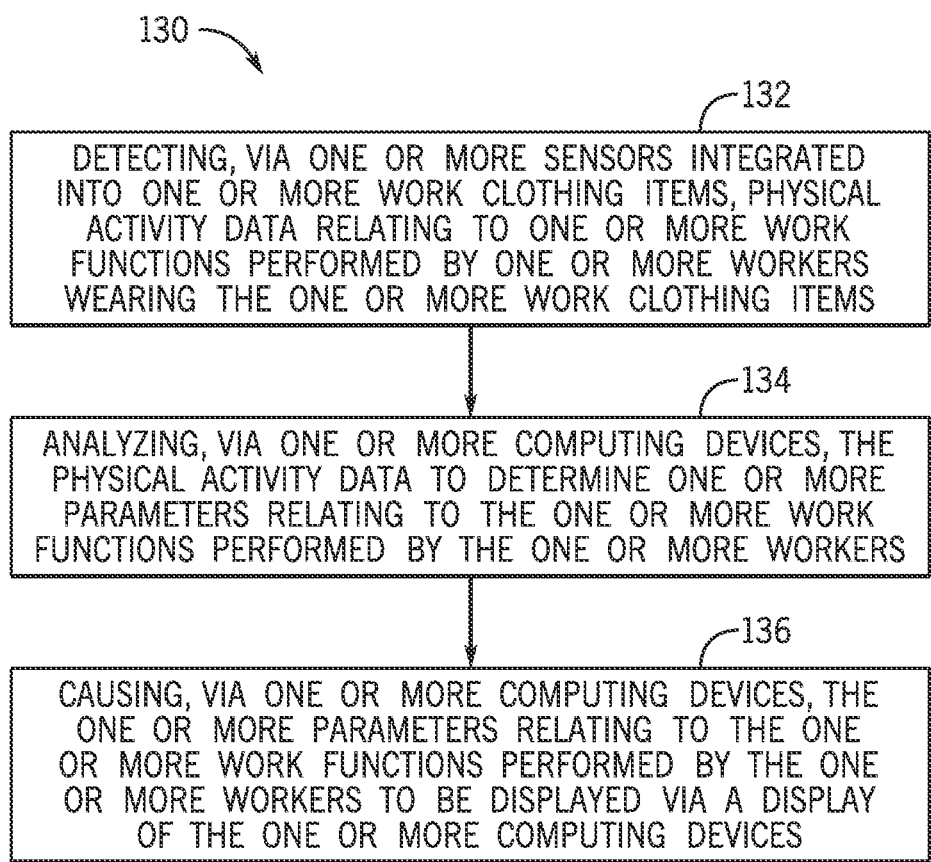

130

132

DETECTING, VIA ONE OR MORE SENSORS INTEGRATED INTO ONE OR MORE WORK CLOTHING ITEMS, PHYSICAL ACTIVITY DATA RELATING TO ONE OR MORE WORK FUNCTIONS PERFORMED BY ONE OR MORE WORKERS WEARING THE ONE OR MORE WORK CLOTHING ITEMS

134

ANALYZING, VIA ONE OR MORE COMPUTING DEVICES, THE PHYSICAL ACTIVITY DATA TO DETERMINE ONE OR MORE PARAMETERS RELATING TO THE ONE OR MORE WORK FUNCTIONS PERFORMED BY THE ONE OR MORE WORKERS

136

CAUSING, VIA ONE OR MORE COMPUTING DEVICES, THE ONE OR MORE PARAMETERS RELATING TO THE ONE OR MORE WORK FUNCTIONS PERFORMED BY THE ONE OR MORE WORKERS TO BE DISPLAYED VIA A DISPLAY OF THE ONE OR MORE COMPUTING DEVICES

FIG. 15

SYSTEMS AND METHODS FOR TRACKING PHYSICAL WORK ACTIVITY

TECHNICAL FIELD

The present disclosure relates generally to systems and methods for tracking physical work activity for the purpose of enabling effective work activity analysis and management.

BACKGROUND

This section is intended to introduce the reader to various aspects of art that may be related to various aspects of the present disclosure, which are described below. This discussion is believed to be helpful in providing the reader with background information to facilitate a better understanding of the various aspects of the present disclosure. Accordingly, it should be understood that these statements are to be read in this light, and not as admissions of prior art.

Managers of employees are often quite interested in how well the employees are performing certain work functions. For example, in situations where the work functions include physical activity, the managers may be interested in ensuring that the employees perform their work functions in as safe and efficient a manner as possible. However, it is often very difficult, if not impossible for some managers to watch all employees performing all of their work functions.

BRIEF DESCRIPTION

Certain embodiments of the present disclosure include a work clothing item that includes one or more sensors integrated into the work clothing item. The one or more sensors are configured to detect physical activity data relating to one or more work functions performed by a worker wearing the work clothing item. The work clothing item also includes communication circuitry configured to transmit the detected physical activity data to a computing device for analysis of the detected physical activity data. The work clothing item further includes a rechargeable battery configured to provide power to the one or more sensors and the communication circuitry.

Certain embodiments of the present disclosure also include a method that includes detecting, via one or more sensors integrated into one or more work clothing items, physical activity data relating to one or more work functions performed by one or more workers wearing the one or more work clothing items. The method also includes analyzing, via one or more computing devices, the physical activity data to determine one or more parameters relating to the one or more work functions performed by the one or more workers. The method further includes causing, via one or more computing devices, the one or more parameters relating to the one or more work functions performed by the one or more workers to be displayed via a display of the one or more computing devices.

Certain embodiments of the present disclosure also include a work activity analysis system that includes one or more processors configured to execute computer-executable instructions, wherein the instructions, when executed by the one or more processors, cause the one or more processors to receive physical activity data relating to one or more work functions performed by one or more workers from one or more work clothing items worn by the one or more workers; to analyze the physical activity data to determine one or more parameters relating to the one or more work functions performed by the one or more workers; and to display the one or more parameters relating to the one or more work functions performed by the one or more workers via a display of the work activity analysis system.

It is appreciated that implementations in accordance with the present disclosure can include any combination of the aspects and features described herein. That is, implementations in accordance with the present disclosure are not limited to the combinations of aspects and features specifically described herein, but also include any other appropriate combinations of the aspects and features provided.

BRIEF DESCRIPTION OF THE DRAWINGS

These and other features, aspects, and advantages of the present disclosure will become better understood when the following detailed description is read with reference to the accompanying drawings in which like characters represent like parts throughout the drawings, wherein:

FIG. 15 is a flow diagram of a method of use of the work activity analysis and management system of FIG. 1, in accordance with embodiments described herein.

DETAILED DESCRIPTION

Figure 1:
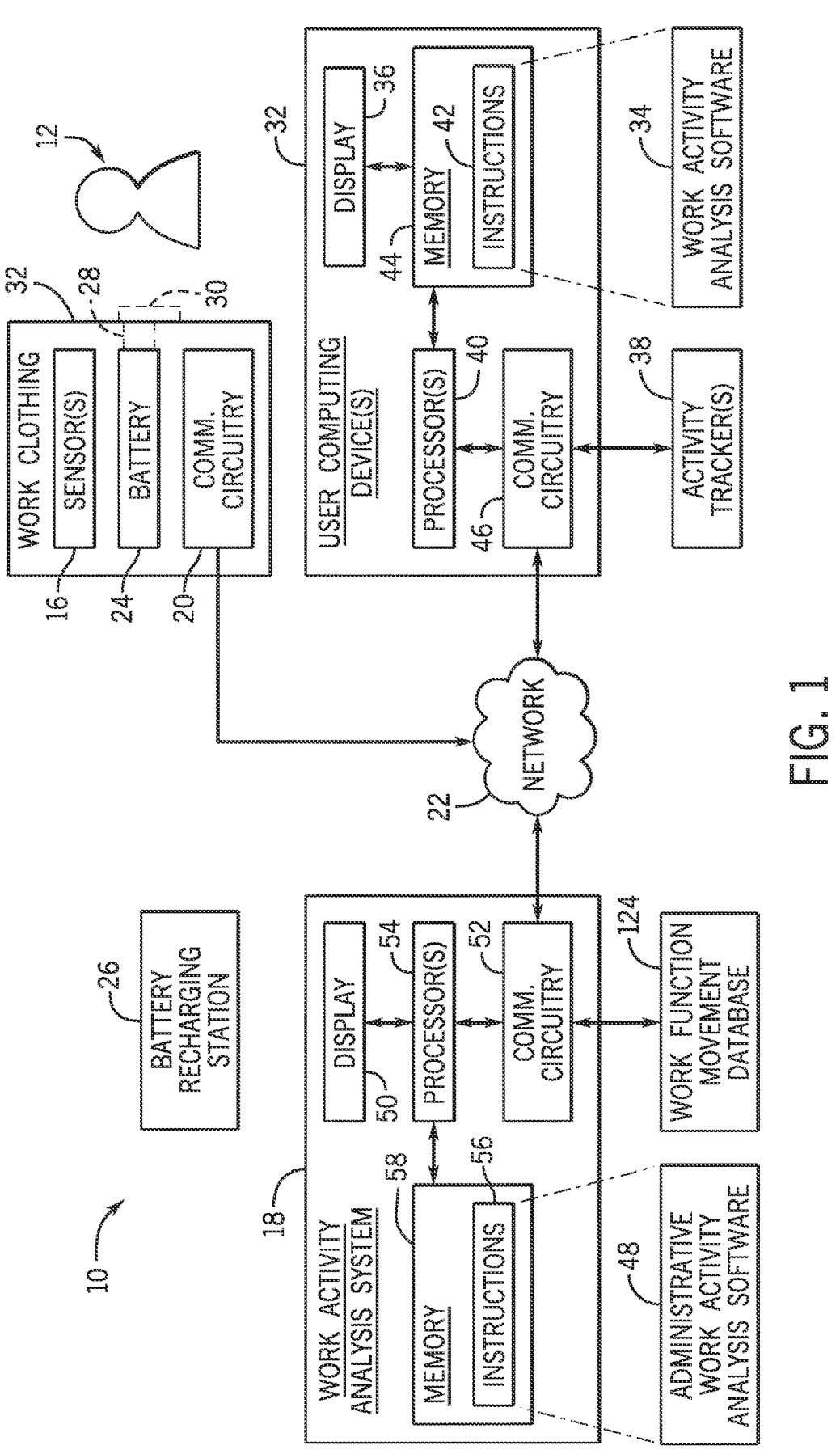
FIG. 1 is a schematic diagram of a work activity analysis and management system configured to track physical activities of workers for the purpose of enabling effective work activity analysis and management, in accordance with embodiments described herein.

One or more specific embodiments will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present disclosure, the articles "a," "an," and "the" are intended to mean that there are one or more of the elements. The terms "comprising," "including," and "having" are intended to be inclusive and mean that there may be additional elements other than the listed elements. Additionally, it should be understood that references to "one embodiment" or "an embodiment" of the present disclosure are not intended to be interpreted as excluding the existence of additional embodiments that also incorporate the recited features.

In the following description, for the purposes of explanation, numerous specific details are set forth in order to provide a thorough understanding of embodiments of the present disclosure. It will be apparent, however, to one skilled in the art that embodiments of the present disclosure may be practiced without some of these specific details.

The embodiments described herein include systems and methods for tracking physical work activity for the purpose of enabling effective work activity analysis and management. For example, the embodiments described herein facilitate work activity tracking by, for example, embedding sensors in items of work clothing, such as work footwear (e.g., work boots, work shoes, and so forth), work socks, work pants, work jackets, work overalls, work belts, work goggles, hard hats, work gloves, and so forth. The sensors embedded in the work clothing may help identify work activity that is not possible by conventional activity trackers, such as dedicated activity trackers (e.g., Fitbit devices), smart watches, and other wearable devices specifically, or at least primarily, dedicated to tracking physical activity. As but one no-limiting example, by embedding pressure sensing devices into "smart shoes", physical activity relating to laziness, inactivity, obesity, heavy lifting, and so forth, relating to workers wearing the smart shoes may be monitored. In certain embodiments, the data collected by the work clothing sensors may be used in combination to other activity data for example, as collected by the conventional activity trackers described above. For example, the smart shoes described above may be used to supplement activity tracker data to, for example, confirm steps, paths, locations and so forth.

In addition, as described in greater detail herein, certain motions relating to certain work activities may be detected and analyzed to, for example, make sure that workers are performing certain work functions in an efficient manner (or, even whether they are performing them at all). In addition, certain types of work clothing (e.g., certain types of work shoes) worn by workers may provide more insight into the behavior of the workers. For example, certain types of work shoes may indicate the performance of certain work functions, whereas other types of work shoes may indicate the performance of other work functions, insofar as the types of work shoes may only be appropriate for certain types of work functions.

In addition, embedding sensors into work clothing may provide additional beneficial information for workers wearing the work clothing. For example, sensor-enabled work clothing may enable the provision of indications to workers regarding how long they are standing per day, an indication of blood flow in their limbs throughout the day, and so forth. In addition, sensor-enabled work clothing may enable the provision of an indication of an amount of wear on the work clothing, as well as when the workers may want to replace the work clothing. In addition, sensor-enabled work clothing may enable the provision of recommendations relating to supplemental work clothing (e.g., recommending inserts for certain types of work footwear), warnings relating to potential health hazards (e.g., blisters), warnings relating to possible overexertion, and so forth.

FIG. 1 is a schematic diagram of a work activity analysis and management system 10 configured to track physical activities of workers 12 for the purpose of enabling effective work activity analysis and management. In particular, in certain embodiments, one or more items of work clothing 14 may be configured to detect certain physical activity of one or more workers 12 such as certain work activities that are performed by the one or more workers 12. In particular, as described in greater detail herein, the one or more items of work clothing 14 may each include one or more sensors 16 embedded within (e.g., integrated into) configured to detect certain physical activity of one or more workers 12, which may be used by an work activity analysis system 18 to facilitate the work activity analysis and management described herein. As described in greater detail herein, in certain embodiments, the items of work clothing 14 may be work footwear (e.g., work boots, work shoes, and so forth), work socks, work pants, work jackets, work overalls, work belts, work goggles, hard hats, work gloves, and other suitable types of work clothing 14. Although described primarily herein as tracking physical work activity related to work functions performed by a worker 12 (e.g., who works for an employer), in other embodiments, the tracked physical work activity may be for work functions performed at home or in other non-work-related scenarios.

In certain embodiments, the one or more items of work clothing 14 may include one or more position/orientation sensors 16 configured to detect positions, orientations, and/or movements of certain parts of a body of a worker 12 wearing the work clothing 14. In addition, in certain embodiments, the one or more items of work clothing 14 may include a global positioning sensor 16, which may be used to detect a global position of a worker 12 wearing the work clothing 14 to, for example, enable the work activity analysis system 18 to determine a specific work location at which the worker 12 wearing the work clothing 14 is currently located. In addition, in certain embodiments, the one or more items of work clothing 14 may include one or more physiological sensors 16 such as heart rate sensors, blood pressure sensors, electrocardiogram sensors, oxygen saturation sensors, stress tracking sensors, or other sensors configured to detect certain physiological parameters of a worker 12 wearing the work clothing 14. In addition, in certain embodiments, the one or more items of work clothing 14 may include one or more temperature sensors 16 configured to, for example, detect a temperature of skin of a worker 12 wearing the work clothing 14, detect an ambient temperature in the vicinity of the worker 12 wearing the work clothing 14, and so forth. In addition, in certain embodiments, the one or more items of work clothing 14 may include one or more moisture sensors 16 to, for example, detect moisture (e.g., representative of the pressure and/or amount of sweat) on the skin of a worker 12 wearing the work clothing 14.

In addition, in certain embodiments, the items of work clothing 14 may include communication circuitry 20 configured to facilitate communication between the items of work clothing 14 and the work activity analysis system 18 via a communication network 22. For example, as described in greater detail herein, in certain embodiments, the items of work clothing 14 may send data relating to the detected activity to the work activity analysis system 18 to facilitate the work activity analysis and management described herein. In certain embodiments, the communication circuitry 20 may facilitate communications using Wi-Fi, near field communication, Bluetooth, Zigbee, radio frequency identification (RFID) tags and/or readers, an embedded wireless module, and/or another suitable wired or wireless communication network 22.

In addition, in certain embodiments, the items of work clothing 14 may include a rechargeable battery 24 configured to provide power to the sensors 16 and the communication circuitry 20 of the work clothing 14. For example, in certain embodiments, the rechargeable battery 24 may be configured to be wirelessly charged when brought into close proximity to (e.g., within two feet of, within one foot of, within 6 includes of, or even closer to) a battery recharging station 26 that, for example, may be located at a worksite at which the associated worker 12 is working. In other embodiments, the rechargeable battery 24 may include a charging connector 28 (e.g., that is exposed at an exterior location of the respective work clothing 14) configured to directly physically couple the rechargeable battery 24 to the battery recharging station 26. In such embodiments, the respective work clothing 14 may include a flap 30 configured to cover the charging connector 28 when the rechargeable battery 24 is not directly physically coupled to the battery recharging station 26. In certain embodiments, the charging connector 28 may include a port extending into the work clothing 14 at an exterior surface of the work clothing 14, wherein the port is configured to receive a mating recharging plug and/or connector end of a recharging cable of the battery recharging station 26 to provide power from the battery recharging station 26 to the one or more sensors 16 and the communication circuitry 20 of the work clothing 14. However, in other embodiments, the charging connector 28 may include a plug extending from an exterior surface of the work clothing 14 and configured to be received by a mating recharging port of the battery recharging station 26 to provide power from the battery recharging station 26 to the one or more sensors 16 and the communication circuitry 20 of the work clothing 14.

In addition, in certain embodiments, one or more user computing devices 32 (e.g., associated with a particular worker 12) may be configured to facilitate detection of certain physical activity of workers 12 associated with the user computing devices 32, as well as to enable the workers 12 to view and analyze information relating to the detected physical activity, for example, via work activity analysis software 34 being executed on the user computing devices 32 (e.g., viewable via displays 36 of the user computing devices 32). For example, in certain embodiments, one or more items of work clothing 14, as well as one or more additional dedicated activity trackers 38 (e.g., Fitbit devices, smart watches, and other wearable devices), associated with a particular worker 12 may be registered with (e.g., synchronized to) a particular user computing device 32 associated with the particular worker 12 such that physical activity data detected by the sensors 16 of the work clothing 14 and/or the additional dedicated activity trackers 38 associated with the particular worker 12 may be collected and synchronized by the particular user computing device 32 and, in certain embodiments, communicated to the work activity analysis system 18 for additional analysis (e.g., in addition to analysis that may be locally performed by the particular user computing device 32). In certain embodiments, the workers 12 may login to particular user computing devices 32 such that worker identifiers (e.g., social security numbers, employee identification numbers, and so forth) may be tracked to associate detected physical activity data with the particular worker 12. In general, in certain embodiments, the work activity analysis software 34 may be configured to analyze the physical activity data for the particular worker 12 to, for example, determine if the particular worker 12 is performing certain work functions properly (or, even, at all), to provide guidance for the particular worker 12 to perform the certain work functions more properly, and so forth, as described in greater detail herein. In certain embodiments, the user computing devices 32 may be smartphones, tablet computers, laptop computers, or any other user computing devices 32 suitable for facilitating the collection of physical activity data detected with respect to workers 12 associated with the user computing devices 32.

In certain embodiments, the user computing devices 32 may include other processing circuitry such as one or more processors 40 configured to execute instructions 42 stored in memory media 44 of the respective user computing device 32, wherein the instructions 42, when executed by the one or more processors 40, enable the respective user computing device 32 to collect and analyze physical activity data associated with a worker 12 associated with the respective user computing device 32 (e.g., as detected by the sensors 16 of the work clothing 14 and/or the additional dedicated activity trackers 38 associated with the worker 12), as described herein.

In certain embodiments, the one or more processors 40 of the user computing devices 32 may be any suitable type of computer processors or microprocessors capable of executing computer-executable code. In certain embodiments, the memory media 44 of the user computing devices 32 may be any suitable articles of manufacture that can serve as media to store processor-executable code, data, or the like. These articles of manufacture may represent computer-readable media (e.g., any suitable form of memory or storage) that may store processor-executable code (e.g., the instructions 42) executed by the one or more processors 40 to perform the presently disclosed techniques. In certain embodiments, the memory media 44 of the user computing devices 32 may represent tangible, non-transitory computer-readable media (e.g., any suitable form of memory or storage) that may store the processor-executable code used by the one or more processors 40 to perform various techniques described herein. It should be noted that non-transitory merely indicates that the media is tangible and not a signal. It should be noted that the components described above with regard to the user computing devices 32 are exemplary components, and the user computing devices 32 may include additional or fewer components in certain embodiments.

In addition, in certain embodiments, the user computing devices 32 may include communication circuitry 46 configured to facilitate communication between the respective user computing device 32 and the work activity analysis system 18, as well as between the respective user computing device 32 and the work clothing 14 and/or the additional dedicated activity trackers 38 associated with a worker 12 associated with the respective user computing device 32. For example, in certain embodiments, the user computing devices 32 may send data relating to detected physical activity for the worker 12 to the work activity analysis system 18 to facilitate the work activity analysis and management described herein. In certain embodiments, the communication circuitry 46 may facilitate communications using Wi-Fi, near field communication, Bluetooth, Zigbee, radio frequency identification (RFID) tags and/or readers, an embedded wireless module, and/or another suitable wired or wireless communication network 22.

In response to receiving data relating to detected physical activity of a worker 12 from one or more user computing devices 32 associated with the worker 12 and/or directly from items of work clothing 14 and/or additional dedicated activity trackers 38 associated with the worker 12, the work activity analysis system 18 may utilize administrative work activity analysis software 48 (e.g., viewable via a display 50 of the work activity analysis system 18) to analyze the physical activity data for the worker 12 to, for example, determine if the worker 12 is performing certain work functions properly (or, even, at all), to provide guidance for the worker 12 to perform the certain work functions more properly, and so forth, as described in greater detail herein. In general, in certain embodiments, the administrative work activity analysis software 48 may be substantially similar to the work activity analysis software 34 installed on the user computing devices 32. However, the administrative work activity analysis software 48 may include additional functionality to, for example, enable a supervising worker 12 to monitor and analyze physical activity data of more than one worker 12, as opposed to the work activity analysis software 34, which may only enable a particular worker 12 to monitor and analyze physical activity data of the particular worker 12. In addition, in certain embodiments, the administrative work activity analysis software 48 (and/or the work activity analysis system 18 itself) may function as a server for performance of more processing-intensive analysis tasks, and results of this processing-intensive analysis may be provided to the work activity analysis software 34 as a client.

In certain embodiments, the work activity analysis system 18 may include communication circuitry 52 configured to facilitate communication between the work activity analysis system 18 and the user computing devices 32, as well as between the work activity analysis system 18 and the work clothing 14 and/or the additional dedicated activity trackers 38 in certain embodiments, as described in greater detail herein. For example, as described in greater detail herein, in certain embodiments, the work activity analysis system 18 may receive data relating to physical activity of workers 12 from one or more user computing devices 32 and/or directly from one or more items of work clothing 14 and/or one or more additional dedicated activity trackers 38 associated with certain workers 12 via the communication network 22, and may automatically (e.g., without human intervention) send notifications to the workers 12 via respective user computing devices 32 to notify the workers 12 of analysis performed by the work activity analysis system 18, as described herein. In certain embodiments, the communication circuitry 52 may facilitate communications using Wi-Fi, near field communication, Bluetooth, Zigbee, radio frequency identification (RFID) tags and/or readers, an embedded wireless module, and/or another suitable wired or wireless communication network 22.

In certain embodiments, the work activity analysis system 18 may include other processing circuitry such as one or more processors 54 configured to execute instructions 56 stored in memory media 58 of the work activity analysis system 18, wherein the instructions 56, when executed by the one or more processors 54, enable the administrative work activity analysis software 48 to perform the functions described in greater detail herein. In certain embodiments, the one or more processors 54 of the work activity analysis system 18 may be any suitable type of computer processors or microprocessors capable of executing computer-executable code. In certain embodiments, the memory media 58 of the work activity analysis system 18 may be any suitable articles of manufacture that can serve as media to store processor-executable code, data, or the like. These articles of manufacture may represent computer-readable media (e.g., any suitable form of memory or storage) that may store processor-executable code (e.g., the instructions 56) executed by the one or more processors 54 to perform the presently disclosed techniques. In certain embodiments, the memory media 58 of the work activity analysis system 18 may also be used to store data relating to physical activity of workers 12, which are detected by the items of work clothing 14 and/or the additional dedicated activity trackers 38, as described in greater detail herein. In certain embodiments, the memory media 58 of the work activity analysis system 18 may represent tangible, non-transitory computer-readable media (e.g., any suitable form of memory or storage) that may store the processor-executable code used by the one or more processors 54 to perform various techniques described herein. It should be noted that non-transitory merely indicates that the media is tangible and not a signal. It should be noted that the components described above with regard to the work activity analysis system 18 are exemplary components, and the work activity analysis system 18 may include additional or fewer components in certain embodiments.

Figure 2:
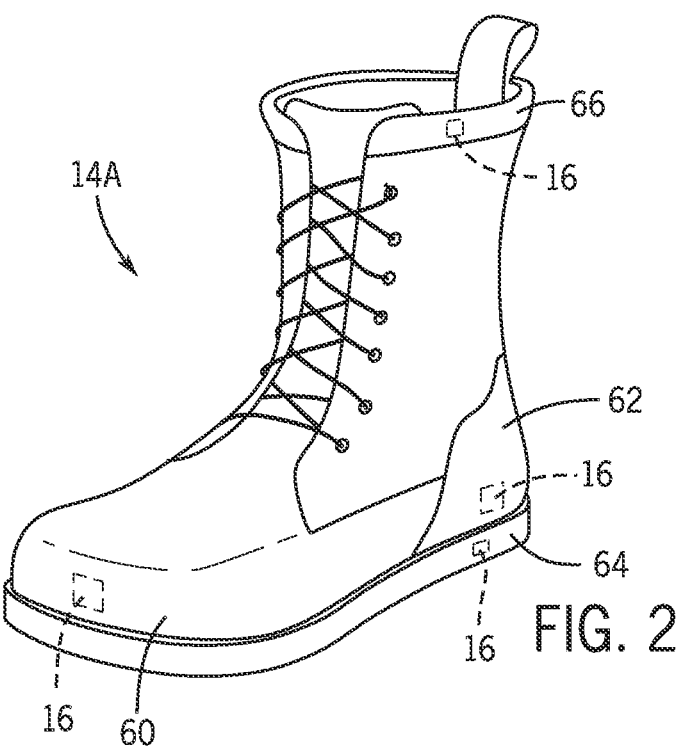
FIG. 2 illustrates example work footwear that may be used as an item of work clothing having one or more sensors embedded (e.g., integrated) therein, in accordance with embodiments described herein.

As described in greater detail herein, certain items of work clothing 14 may have one or more sensors 16, as well as communication circuitry 20 and a rechargeable battery 24, embedded within (e.g., integrated into) the work clothing 14 to facilitate detecting data relating to physical work activity related to certain work functions performed by workers 12 wearing the work clothing 14. For example, FIG. 2 illustrates example work footwear 14A (e.g., a work boot, a work shoe, and so forth) that may be used as an item of work clothing 14 having one or more sensors 16 embedded (e.g., integrated) therein. As illustrated in FIG. 2, in certain embodiments, position/orientation sensors 16 may be embedded within (e.g., integrated into) one or more various portions of the work footwear 14A including, but not limited to, a toe portion 60 of the work footwear 14A, a heel portion 62 of the work footwear 14A, a sole portion 64 of the work footwear 14A, a cuff (e.g., pull strap) portion 66 of the work footwear 14A, and so forth.

In addition, although not illustrated in FIG. 2 (for simplicity of illustration), it will be appreciated that the communication circuitry 20 and the rechargeable battery 24 of the work footwear 14A may be similarly embedded within (e.g., integrated into) the various portions of the work footwear 14A including, but not limited to, the toe portion 60 of the work footwear 14A, the heel portion 62 of the work footwear 14A, the sole portion 64 of the work footwear 14A, the cuff (e.g., pull strap) portion 66 of the work footwear 14A, and so forth. In addition, although not illustrated in FIG. 2, in certain embodiments, the work footwear 14A may include relatively thin electrical wire (e.g., 28 gauge, 32, gauge, 40 gauge, and so forth) embedded within (e.g., integrated into) the work footwear 14A to electrically connect the position/orientation sensors 16, the communication circuitry 20, and the rechargeable battery 24 in instances where they are not directly adjacent each other (e.g., when they are located in different portions of the work footwear 14A).

As described in greater detail herein, the one or more position/orientation sensors 16 of the work footwear 14A may detect position, orientation, and/or movement of the respective portions of the work footwear 14A, which may be indicative of certain physical work activity associated with certain work activities performed by a worker 12 wearing the work footwear 14A. Once the physical work activity data is detected by the one or more position/orientation sensors 16, the communication circuitry 20 of the work footwear 14A may transmit the detected physical work activity data to one or more computing devices (e.g., the work activity analysis system 18 and/or one or more user computing devices 32) for analysis, as described in greater detail herein.

Figure 3:
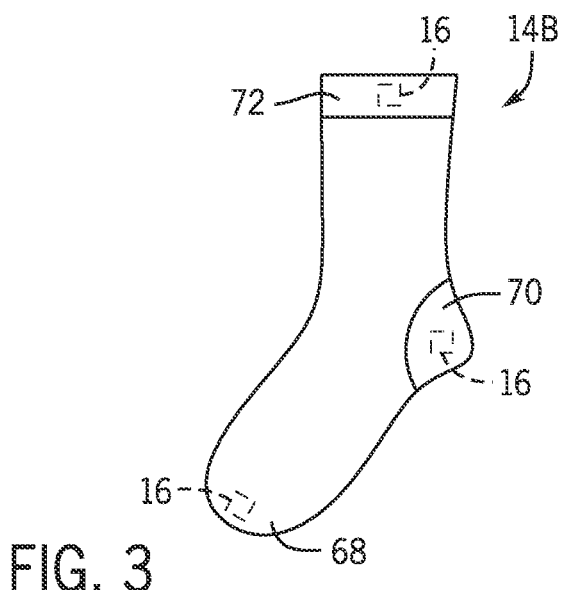
FIG. 3 illustrates an example work sock that may be used as an item of work clothing having one or more sensors embedded (e.g., integrated) therein, in accordance with embodiments described herein.

In addition, FIG. 3 illustrates an example work sock 14B that may be used as an item of work clothing 14 having one or more sensors 16 embedded (e.g., integrated) therein. As illustrated in FIG. 3, in certain embodiments, position/orientation sensors 16 may be embedded within (e.g., integrated into) one or more various portions of the work sock 14B including, but not limited to, a toe portion 68 of the work sock 14B, a heel portion 70 of the work sock 14B, a cuff portion 72 of the work sock 14B, and so forth.

In addition, although not illustrated in FIG. 3 (for simplicity of illustration), it will be appreciated that the communication circuitry 20 and the rechargeable battery 24 of the work sock 14B may be similarly embedded within (e.g., integrated into) the various portions of the work sock 14B including, but not limited to, the toe portion 68 of the work sock 14B, the heel portion 70 of the work sock 14B, the cuff portion 72 of the work sock 14B, and so forth. In addition, although not illustrated in FIG. 3, in certain embodiments, the work sock 14B may include relatively thin electrical wire (e.g., 28 gauge, 32, gauge, 40 gauge, and so forth) embedded within (e.g., integrated into) the work sock 14B to electrically connect the position/orientation sensors 16, the communication circuitry 20, and the rechargeable battery 24 in instances where they are not directly adjacent each other (e.g., when they are located in different portions of the work sock 14B).

As described in greater detail herein, the one or more position/orientation sensors 16 of the work sock 14B may detect position, orientation, and/or movement of the respective portions of the work sock 14B, which may be indicative of certain physical work activity associated with certain work activities performed by a worker 12 wearing the work sock 14B. Once the physical work activity data is detected by the one or more position/orientation sensors 16, the communication circuitry 20 of the work sock 14B may transmit the detected physical work activity data to one or more computing devices (e.g., the work activity analysis system 18 and/or one or more user computing devices 32) for analysis, as described in greater detail herein.

Figure 4:
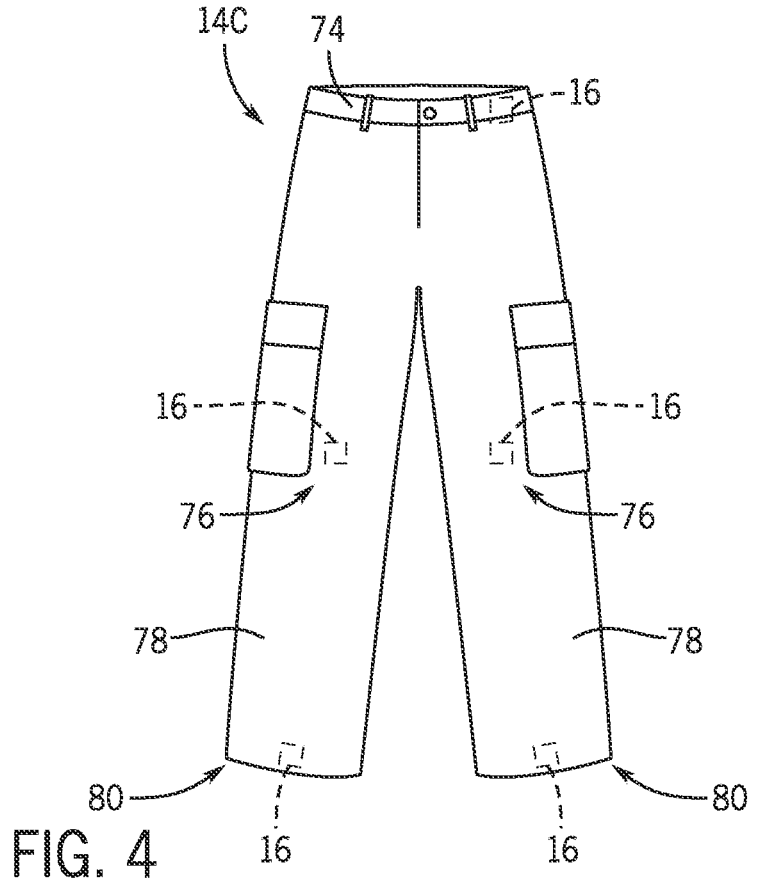
FIG. 4 illustrates an example pair of work pants that may be used as an item of work clothing having one or more sensors embedded (e.g., integrated) therein, in accordance with embodiments described herein.

In addition, FIG. 4 illustrates an example pair of work pants 14C that may be used as an item of work clothing 14 having one or more sensors 16 embedded (e.g., integrated) therein. As illustrated in FIG. 4, in certain embodiments, position/orientation sensors 16 may be embedded within (e.g., integrated into) one or more various portions of the work pants 14C including, but not limited to, a waistline portion 74 of the work pants 14C, a knee portion 76 of one or more legs 78 of the work pants 14C, a bottom hem portion 80 of the one or more legs 78 of the work pants 14C, and so forth.

In addition, although not illustrated in FIG. 4 (for simplicity of illustration), it will be appreciated that the communication circuitry 20 and the rechargeable battery 24 of the work pants 14C may be similarly embedded within (e.g., integrated into) the various portions of the work pants 14C including, but not limited to, the waistline portion 74 of the work pants 14C, the knee portion 76 of one or more legs 78 of the work pants 14C, the bottom hem portion 80 of the one or more legs 78 of the work pants 14C, and so forth. In addition, although not illustrated in FIG. 4, in certain embodiments, the work pants 14C may include relatively thin electrical wire (e.g., 28 gauge, 32, gauge, 40 gauge, and so forth) embedded within (e.g., integrated into) the work pants 14C to electrically connect the position/orientation sensors 16, the communication circuitry 20, and the rechargeable battery 24 in instances where they are not directly adjacent each other (e.g., when they are located in different portions of the work pants 14C).

As described in greater detail herein, the one or more position/orientation sensors 16 of the work pants 14C may detect position, orientation, and/or movement of the respective portions of the work pants 14C, which may be indicative of certain physical work activity associated with certain work activities performed by a worker 12 wearing the work pants 14C. For example, a position/orientation sensor 16 embedded within (e.g., integrated into) the waistline portion 74 of the work pants 14C may detect a particular position and orientation, which may be used as a baseline position and orientation to determine relative position, orientation, and/or movement of various portions of the legs 78 of the work pants 14C to, for example, determine a three-dimensional recreation of position, orientation, and/or movement of the entire legs 78 of the work pants 14C over time, which may be further analyzed, as described in greater detail herein. Once the physical work activity data is detected by the one or more position/orientation sensors 16, the communication circuitry 20 of the work pants 14C may transmit the detected physical work activity data to one or more computing devices (e.g., the work activity analysis system 18 and/or one or more user computing devices 32) for analysis, as described in greater detail herein.

Figure 5:
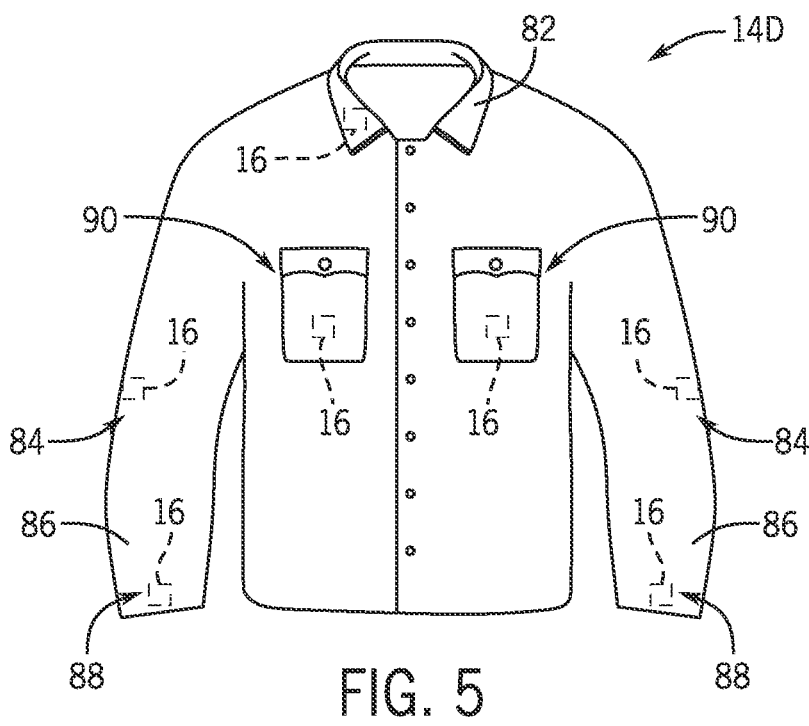
FIG. 5 illustrates an example work jacket that may be used as an item of work clothing having one or more sensors embedded (e.g., integrated) therein, in accordance with embodiments described herein.

In addition, FIG. 5 illustrates an example work jacket 14D that may be used as an item of work clothing 14 having one or more sensors 16 embedded (e.g., integrated) therein. As illustrated in FIG. 5, in certain embodiments, position/orientation sensors 16 may be embedded within (e.g., integrated into) one or more various portions of the work jacket 14D including, but not limited to, a neckline portion 82 of the work jacket 14D, an elbow portion 84 of one or more arms 86 of the work jacket 14D, a cuff portion 88 of the one or more arms 86 of the work jacket 14D, a breast portion 90 of the work jacket 14D, and so forth.

In addition, although not illustrated in FIG. 5 (for simplicity of illustration), it will be appreciated that the communication circuitry 20 and the rechargeable battery 24 of the work jacket 14D may be similarly embedded within (e.g., integrated into) the various portions of the work jacket 14D including, but not limited to, the neckline portion 82 of the work jacket 14D, the elbow portion 84 of one or more arms 86 of the work jacket 14D, the cuff portion 88 of the one or more arms 86 of the work jacket 14D, the breast portion 90 of the work jacket 14D, and so forth. In addition, although not illustrated in FIG. 5, in certain embodiments, the work jacket 14D may include relatively thin electrical wire (e.g., 28 gauge, 32, gauge, 40 gauge, and so forth) embedded within (e.g., integrated into) the work jacket 14D to electrically connect the position/orientation sensors 16, the communication circuitry 20, and the rechargeable battery 24 in instances where they are not directly adjacent each other (e.g., when they are located in different portions of the work jacket 14D).

As described in greater detail herein, the one or more position/orientation sensors 16 of the work jacket 14D may detect position, orientation, and/or movement of the respective portions of the work jacket 14D, which may be indicative of certain physical work activity associated with certain work activities performed by a worker 12 wearing the work jacket 14D. For example, a position/orientation sensor 16 embedded within (e.g., integrated into) the neckline portion 82 or the breast portion 90 of the work jacket 14D may detect a particular position and orientation, which may be used as a baseline position and orientation to determine relative position, orientation, and/or movement of various portions of the arms 86 of the work jacket 14D to, for example, determine a three-dimensional recreation of position, orientation, and/or movement of the entire arms 86 of the work jacket 14D over time, which may be further analyzed, as described in greater detail herein. Once the physical work activity data is detected by the one or more position/orientation sensors 16, the communication circuitry 20 of the work jacket 14D may transmit the detected physical work activity data to one or more computing devices (e.g., the work activity analysis system 18 and/or one or more user computing devices 32) for analysis, as described in greater detail herein.

Figure 6:
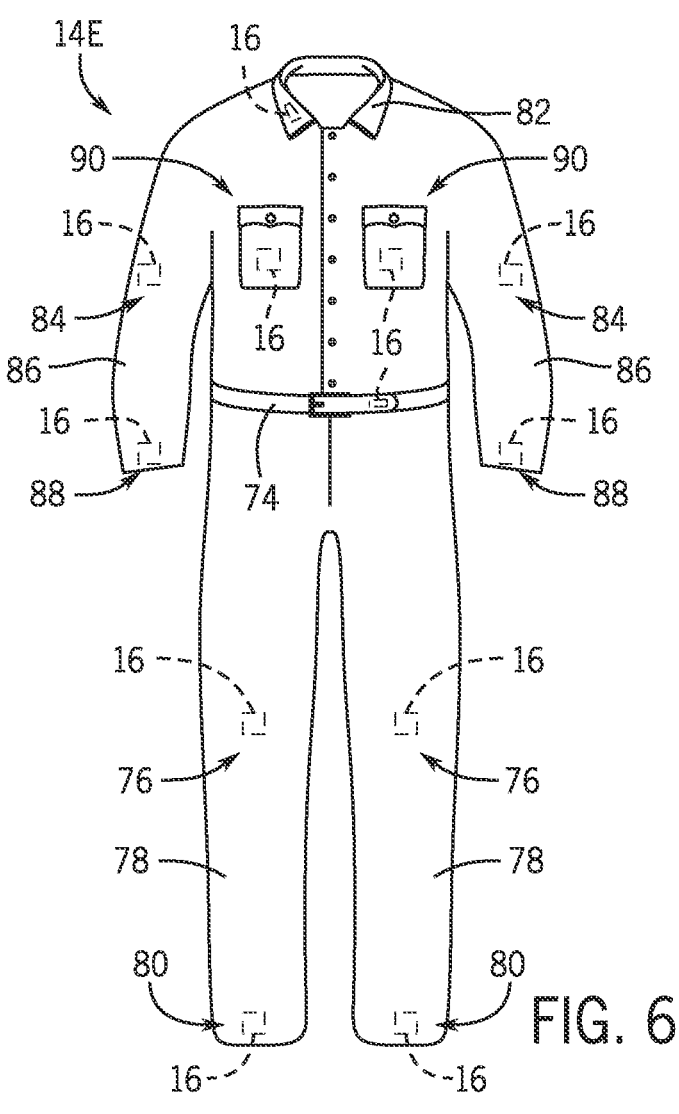
FIG. 6 illustrates an example pair of work overalls that may be used as an item of work clothing having one or more sensors embedded (e.g., integrated) therein, in accordance with embodiments described herein.

In addition, FIG. 6 illustrates an example pair of work overalls 14E that may be used as an item of work clothing 14 having one or more sensors 16 embedded (e.g., integrated) therein. As will be appreciated, the work overalls 14E may generally be substantially similar to a combination of the work pants 14C illustrated in FIG. 4 and the work jacket 14D illustrated in FIG. 5. Indeed, for simplicity, like element numbers are used for the work overalls 14E as with the work pants 14C illustrated in FIG. 4 and the work jacket 14D illustrated in FIG. 5. However, the work overalls 14E will function as a single item of work clothing 14, with all of the position/orientation sensors 16, communication circuitry 20, and rechargeable battery 24 being electrically connected with each other, and functioning together, as described in greater detail herein.

Figure 7:
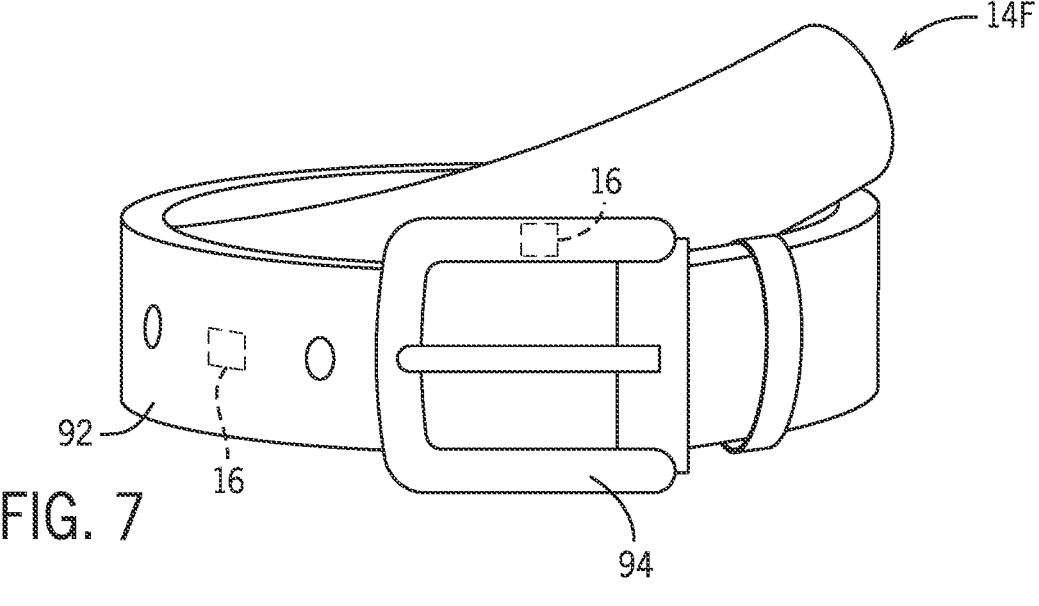
FIG. 7 illustrates an example work belt that may be used as an item of work clothing having one or more sensors embedded (e.g., integrated) therein, in accordance with embodiments described herein.

In addition, FIG. 7 illustrates an example work belt 14F that may be used as an item of work clothing 14 having one or more sensors 16 embedded (e.g., integrated) therein. As illustrated in FIG. 7, in certain embodiments, position/ orientation sensors 16 may be embedded within (e.g., integrated into) one or more various portions of the work belt

14F including, but not limited to, a strap 92 of the work belt 14F, a buckle 94 of the work belt 14F, and so forth.

In addition, although not illustrated in FIG. 7 (for simplicity of illustration), it will be appreciated that the communication circuitry 20 and the rechargeable battery 24 of the work belt 14F may be similarly embedded within (e.g., integrated into) the various portions of the work belt 14F including, but not limited to, the strap 92 of the work belt 14F, the buckle 94 of the work belt 14F, and so forth. In addition, although not illustrated in FIG. 7, in certain embodiments, the work belt 14F may include relatively thin electrical wire (e.g., 28 gauge, 32, gauge, 40 gauge, and so forth) embedded within (e.g., integrated into) the work belt 14F to electrically connect the position/orientation sensors 16, the communication circuitry 20, and the rechargeable battery 24 in instances where they are not directly adjacent each other (e.g., when they are located in different portions of the work belt 14F). In addition, in certain embodiments, the work belt 14F may include electrical contacts (not shown) on both the strap 92 and the buckle 94 of the work belt 14F to enable electrical connection between the strap 92 and the buckle 94 despite the ability of the strap 92 and the buckle 94 to move relative to each other at a point of contact between the strap 92 and the buckle 94.

As described in greater detail herein, the one or more position/orientation sensors 16 of the work belt 14F may detect position, orientation, and/or movement of the respective portions of the work belt 14F, which may be indicative of certain physical work activity associated with certain work activities performed by a worker 12 wearing the work belt 14F. Once the physical work activity data is detected by the one or more position/orientation sensors 16, the communication circuitry 20 of the work belt 14F may transmit the detected physical work activity data to one or more computing devices (e.g., the work activity analysis system 18 and/or one or more user computing devices 32) for analysis, as described in greater detail herein.

Figure 8:
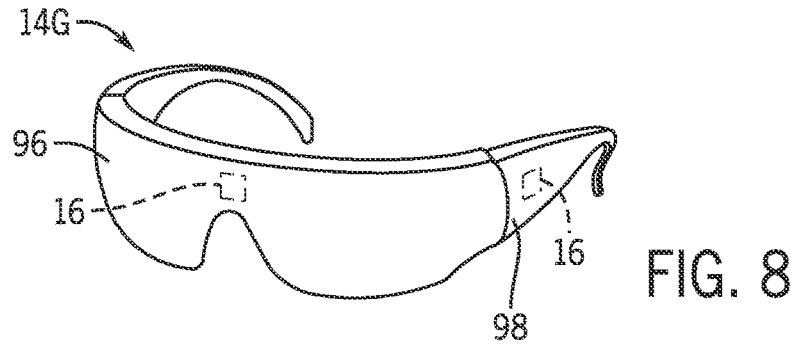
FIG. 8 illustrates an example pair of work goggles that may be used as an item of work clothing having one or more sensors embedded (e.g., integrated) therein, in accordance with embodiments described herein.

In addition, FIG. 8 illustrates an example pair of work goggles 14G that may be used as an item of work clothing 14 having one or more sensors 16 embedded (e.g., integrated) therein. As illustrated in FIG. 8, in certain embodiments, position/orientation sensors 16 may be embedded within (e.g., integrated into) one or more various portions of the work goggles 14G including, but not limited to, a frame 96 of the work goggles 14G, temples 98 of the work goggles 14G, and so forth.

In addition, although not illustrated in FIG. 8 (for simplicity of illustration), it will be appreciated that the communication circuitry 20 and the rechargeable battery 24 of the work goggles 14G may be similarly embedded within (e.g., integrated into) the various portions of the work goggles 14G including, but not limited to, the frame 96 of the work goggles 14G, the temples 98 of the work goggles 14G, and so forth. In addition, although not illustrated in FIG. 8, in certain embodiments, the work goggles 14G may include relatively thin electrical wire (e.g., 28 gauge, 32, gauge, 40 gauge, and so forth) embedded within (e.g., integrated into) the work goggles 14G to electrically connect the position/orientation sensors 16, the communication circuitry 20, and the rechargeable battery 24 in instances where they are not directly adjacent each other (e.g., when they are located in different portions of the work goggles 14G). In addition, in certain embodiments, the work goggles 14G may include electrical contacts (not shown) on both the frame 96 and the temples 98 of the work goggles 14G to enable electrical connection between the frame 96 and the temples 98 despite the ability of the frame 96 and the temples 98 to move relative to each other at a point of contact between the frame 96 and the temples 98.

As described in greater detail herein, the one or more position/orientation sensors 16 of the work goggles 14G may detect position, orientation, and/or movement of the respective portions of the work goggles 14G, which may be indicative of certain physical work activity associated with certain work activities performed by a worker 12 wearing the work goggles 14G. Once the physical work activity data is detected by the one or more position/orientation sensors 16, the communication circuitry 20 of the work goggles 14G may transmit the detected physical work activity data to one or more computing devices (e.g., the work activity analysis system 18 and/or one or more user computing devices 32) for analysis, as described in greater detail herein.

Figure 9:
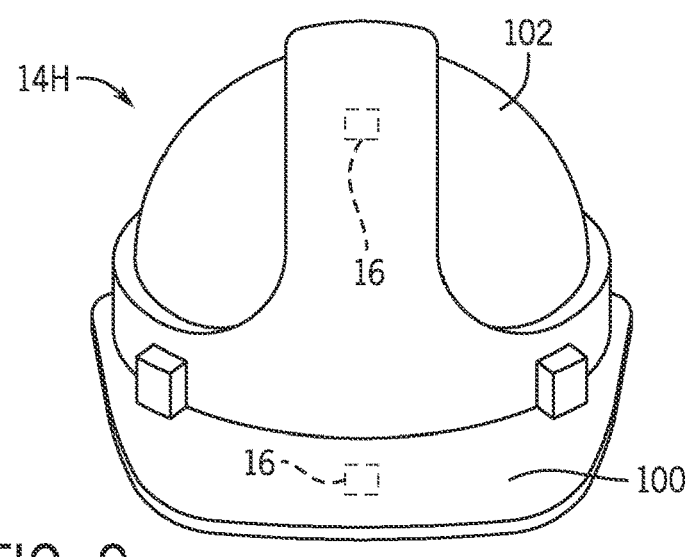
FIG. 9 illustrates an example hard hat that may be used as an item of work clothing having one or more sensors embedded (e.g., integrated) therein, in accordance with embodiments described herein.

In addition, FIG. 9 illustrates an example hard hat 14H that may be used as an item of work clothing 14 having one or more sensors 16 embedded (e.g., integrated) therein. As illustrated in FIG. 9, in certain embodiments, position/orientation sensors 16 may be embedded within (e.g., integrated into) one or more various portions of the hard hat 14H including, but not limited to, a brim 100 of the hard hat 14H, a crown 102 of the hard hat 14H, and so forth.

In addition, although not illustrated in FIG. 9 (for simplicity of illustration), it will be appreciated that the communication circuitry 20 and the rechargeable battery 24 of the hard hat 14H may be similarly embedded within (e.g., integrated into) the various portions of the hard hat 14H including, but not limited to, the brim 100 of the hard hat 14H, the crown 102 of the hard hat 14H, and so forth. In addition, although not illustrated in FIG. 9, in certain embodiments, the hard hat 14H may include relatively thin electrical wire (e.g., 28 gauge, 32, gauge, 40 gauge, and so forth) embedded within (e.g., integrated into) the hard hat 14H to electrically connect the position/orientation sensors 16, the communication circuitry 20, and the rechargeable battery 24 in instances where they are not directly adjacent each other (e.g., when they are located in different portions of the hard hat 14H).

As described in greater detail herein, the one or more position/orientation sensors 16 of the hard hat 14H may detect position, orientation, and/or movement of the respective portions of the hard hat 14H, which may be indicative of certain physical work activity associated with certain work activities performed by a worker 12 wearing the hard hat 14H. Once the physical work activity data is detected by the one or more position/orientation sensors 16, the communication circuitry 20 of the hard hat 14H may transmit the detected physical work activity data to one or more computing devices (e.g., the work activity analysis system 18 and/or one or more user computing devices 32) for analysis, as described in greater detail herein.

Figure 10:
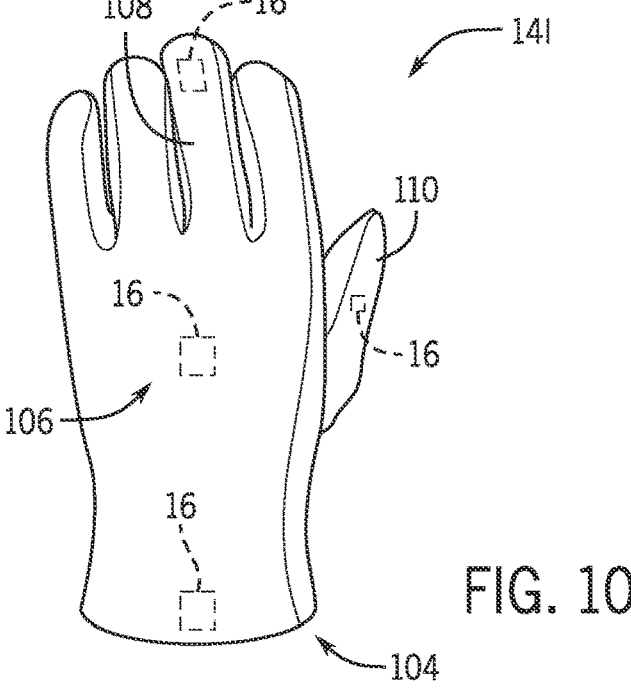
FIG. 10 illustrates an example pair of work gloves that may be used as an item of work clothing having one or more sensors embedded (e.g., integrated) therein, in accordance with embodiments described herein.

In addition, FIG. 10 illustrates an example pair of work gloves 14I that may be used as an item of work clothing 14 having one or more sensors 16 embedded (e.g., integrated) therein. As illustrated in FIG. 10, in certain embodiments, position/orientation sensors 16 may be embedded within (e.g., integrated into) one or more various portions of the work gloves 14I including, but not limited to, a wrist portion 104 of the work gloves 14I, a backside portion 106 (or, alternatively, a palm portion, in other embodiments) of the work gloves 14I, one or more fingers 108 of the work gloves 14I, a thumb 110 of the work gloves 14I, and so forth.

In addition, although not illustrated in FIG. 10 (for simplicity of illustration), it will be appreciated that the communication circuitry 20 and the rechargeable battery 24 of the work gloves 14I may be similarly embedded within (e.g., integrated into) the various portions of the work gloves 14I including, but not limited to, the wrist portion 104 of the work gloves 14I, the backside portion 106 of the work gloves 14I, the one or more fingers 108 of the work gloves 14I, the thumb 110 of the work gloves 14I, and so forth. In addition, although not illustrated in FIG. 10, in certain embodiments, the work gloves 14I may include relatively thin electrical wire (e.g., 28 gauge, 32, gauge, 40 gauge, and so forth) embedded within (e.g., integrated into) the work gloves 14I to electrically connect the position/orientation sensors 16, the communication circuitry 20, and the rechargeable battery 24 in instances where they are not directly adjacent each other (e.g., when they are located in different portions of the work gloves 14I).

As described in greater detail herein, the one or more position/orientation sensors 16 of the work gloves 14I may detect position, orientation, and/or movement of the respective portions of the work gloves 14I, which may be indicative of certain physical work activity associated with certain work activities performed by a worker 12 wearing the work gloves 14I. For example, a position/orientation sensor 16 embedded within (e.g., integrated into) the wrist portion 104 of the work gloves 14I may detect a particular position and orientation, which may be used as a baseline position and orientation to determine relative position, orientation, and/or movement of various portions of the fingers 108 and thumbs 110 of the work gloves 14I to, for example, determine a three-dimensional recreation of position, orientation, and/or movement of the fingers 108 and thumbs 110 of the work gloves 14I over time, which may be further analyzed, as described in greater detail herein. Once the physical work activity data is detected by the one or more position/orientation sensors 16, the communication circuitry 20 of the work gloves 14I may transmit the detected physical work activity data to one or more computing devices (e.g., the work activity analysis system 18 and/or one or more user computing devices 32) for analysis, as described in greater detail herein.

Although described with respect to FIGS. 2 through 10 as including position/orientation sensors 16 configured to detect positions, orientations, and/or movement of certain portions of items of work clothing 14, in certain embodiments, the items of work clothing 14 may additionally, or alternatively, include other types of sensors 16, as described in greater detail herein. For example, in certain embodiments, the one or more items of work clothing 14 may include a global positioning sensor 16, which may be used to detect a global position of a worker 12 wearing the work clothing 14 to, for example, enable the work activity analysis system 18 and/or one or more user computing devices 32 to determine a specific work location at which the worker 12 wearing the work clothing 14 is currently located. In certain embodiments, determination of a specific work location at which the worker 12 is currently located may be used by the work activity analysis system 18 and/or the one or more user computing devices 32 to filter (or, at least adjust a weighting on the probability of) potential work functions against which detected positions, orientations, and/or movements of the worker 12 are being compared, as described in greater detail herein. For example, in certain embodiments, some work functions would not expected to be performed at certain work locations, whereas other work functions might be very commonplace at the certain work locations.

In addition, in certain embodiments, determination of a specific type of item of work clothing 14 being worn by a worker 12 (e.g., as identified by the circuitry of the particular item of work clothing 14) may be used by the work activity analysis system 18 and/or the one or more user computing devices 32 to filter (or, at least adjust a weighting on the probability of) potential work functions against which detected positions, orientations, and/or movements of the worker 12 are being compared, as described in greater detail herein. For example, in certain embodiments, some work functions would not expected to be performed when the worker 12 is wearing certain types of work clothing 14 (e.g., work footwear 14A), whereas other work functions might be very common when the worker 12 is wearing other types of work clothing 14 (e.g., slip-on work shoes, versus work boots).

In addition, in certain embodiments, the one or more items of work clothing 14 may include one or more physiological sensors 16 such as heart rate sensors, blood pressure sensors, electrocardiogram sensors, oxygen saturation sensors, stress tracking sensors, or other sensors configured to detect certain physiological parameters of a worker 12 wearing the work clothing 14. As described in greater detail herein, physiological data detected by the physiological sensors 16 may be used by the work activity analysis system 18 and/or one or more user computing devices 32 to determine if the worker 12 is struggling with certain work functions (or performing certain work functions with relative ease). For example, by comparing heart rates of different workers 12 performing what is determined to be likely the same work function, a determination of which worker 12 is relatively well-suited for the work function may be made.

In addition, in certain embodiments, the one or more items of work clothing 14 may include one or more temperature sensors 16 configured to, for example, detect a temperature of skin of a worker 12 wearing the work clothing 14, detect an ambient temperature in the vicinity of the worker 12 wearing the work clothing 14, and so forth. Similar to the physiological data detected by the physiological sensors 16, temperature data detected by the temperature sensors 16 may also be used by the work activity analysis system 18 and/or one or more user computing devices 32 to determine if the worker 12 is struggling with certain work functions (or performing certain work functions with relative ease). For example, if the skin temperature of the worker 12 gets too high while performing a particular work function, this may be an indication that performance of the particular work function may not be suitable for the worker 12 and/or suitable a particular point at the work location. The ambient temperature in the vicinity of the worker 12 may also provide context for the skin temperature of the worker 12 while performing the particular work function.

In addition, in certain embodiments, the one or more items of work clothing 14 may include one or more moisture sensors 16 to, for example, detect moisture (e.g., representative of the pressure and/or amount of sweat) on the skin of a worker 12 wearing the work clothing 14. Similar to the physiological data detected by the physiological sensors 16, moisture data detected by the moisture sensors 16 may also be used by the work activity analysis system 18 and/or one or more user computing devices 32 to determine if the worker 12 is struggling with certain work functions (or performing certain work functions with relative ease). For example, certain amounts of skin moisture may suggest that the worker 12 is having a relatively difficult time performing a particular work function.

In addition, in certain embodiments, the one or more items of work clothing 14 may include one or more pressure sensors 16 configured to, for example, detect a pressure (e.g., weight, or other force, acting upon) acting upon the pressure sensors 16. For example, in certain embodiments, the pressure sensors 16 may be disposed in sole portions 64 of work footwear 14A to enable the work activity analysis system 18 and/or one or more user computing devices 32 to determine if a worker 12 wearing the work clothing 14 is exhibiting laziness, inactivity, obesity, heavy lifting, and so forth.

In addition, in certain embodiments, the one or more items of work clothing 14 may include one or more audio sensors 16 configured to, for example, detect audio in the vicinity of a worker 12 wearing the work clothing 14. For example, in certain embodiments, the audio sensors 16 may be configured to collect additional data relating to the worker 12 and how (or even if) they are performing their work functions (e.g., if they are spending an inordinate amount of time talking to co-workers, taking breaks, and so forth).

Figures 11, 12:
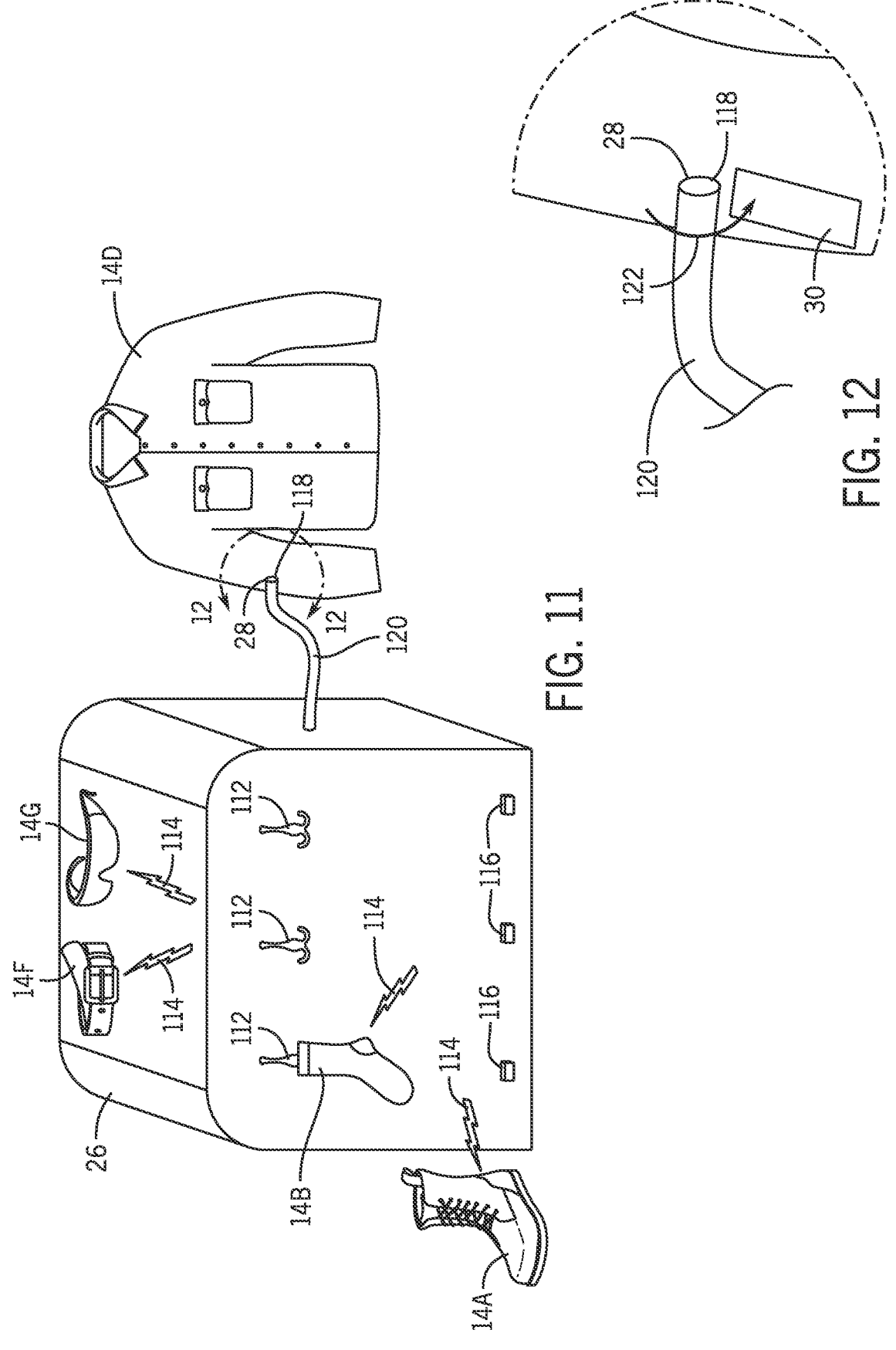
FIG. 11 illustrates various items of work clothing being recharged using a battery recharging station, in accordance with embodiments described herein.
FIG. 12 illustrates a portion of an item of work clothing having a flap to protect a charging connector of the item of work clothing, in accordance with embodiments described herein.

As described above, in certain embodiments, the rechargeable batteries 24 that are associated with the one or more sensors 16 and the communication circuitry 20 of the work clothing 14 described herein may be rechargeable such that they do not need to be removed from the work clothing to be replaced. For example, as illustrated in FIG. 11, in certain embodiments, the rechargeable batteries 24 of the work clothing 14 may be configured to be wirelessly recharged when brought into close proximity to (e.g., within two feet of, within one foot of, within 6 includes of, or even closer to) a battery recharging station 26. For example, as illustrated in FIG. 11, in certain embodiments, one or more items of work clothing 14 may be placed on top of, placed next to, or hung on hooks 112 on the sides of the battery recharging station 26 while the battery recharging station 26 wirelessly recharges the rechargeable batteries 24 within the items of work clothing 14, as illustrated by arrows 114.

However, as also illustrated in FIG. 11, in certain embodiments, the work clothing 14 may include a charging connector 28 electrically connected to the one or more sensors 16 and the communication circuitry 20 of the work clothing 14, wherein the charging connector 28 is configured to directly couple to a mating charging connector of the battery recharging station 26 to provide power from the battery recharging station 26 to the one or more sensors 16 and the communication circuitry 20 of the work clothing 14. For example, in certain embodiments, the charging connector 28 may include a port extending into the work clothing 14 at an exterior surface of the work clothing 14, wherein the port is configured to receive a mating recharging plug 116 and/or connector end 118 of a recharging cable 120 of the battery recharging station 26 to provide power from the battery recharging station 26 to the one or more sensors 16 and the communication circuitry 20 of the work clothing 14. However, in other embodiments, the charging connector 28 may include a plug extending from an exterior surface of the work clothing 14 and configured to be received by a mating recharging port of the battery recharging station 26 to provide power from the battery recharging station 26 to the one or more sensors 16 and the communication circuitry 20 of the work clothing 14.

As illustrated in FIG. 12, in certain embodiments, the work clothing 14 may include a flap 30 (e.g., a strip of fabric) configured to cover the charging connector 28 when the charging connector 28 is not directly physically coupled to the battery recharging station 26, and to be pulled back to expose the charging connector 28 for direct physical coupling to the battery recharging station 26, as illustrated by arrow 122.

As described in greater detail herein, in certain embodiments, the work activity analysis system 18 and/or one or more user computing devices 32 may receive physical activity data from one or more position/orientation sensors 16 of work clothing 14 configured to detect positions, orientations, and/or movements of certain parts of a body of a worker 12 wearing the work clothing 14 and, based on this detected position, orientation, and/or movement data, may recreate three-dimensional physical movements (e.g., of arms, legs, feet, hands, torso, head, and so forth, of the worker 12) performed by the worker 12 while wearing the work clothing 14 (e.g., during a period of time), which may correspond to certain work functions. Then, the work activity analysis system 18 and/or one or more user computing devices 32 may correlate the recreated three-dimensional physical movement patterns with known physical movement patterns relating to certain work functions (e.g., using pattern matching algorithms), which may be stored in a work function movement database 124 (e.g., as illustrated in FIG. 1). In general, the known physical movement patterns relating to certain work functions may be idealized movement patterns that are relatively ideal for the particular work functions to which they relate, and may serve as a goal for the worker(s) 12 performing those particular work functions.

Figure 13:
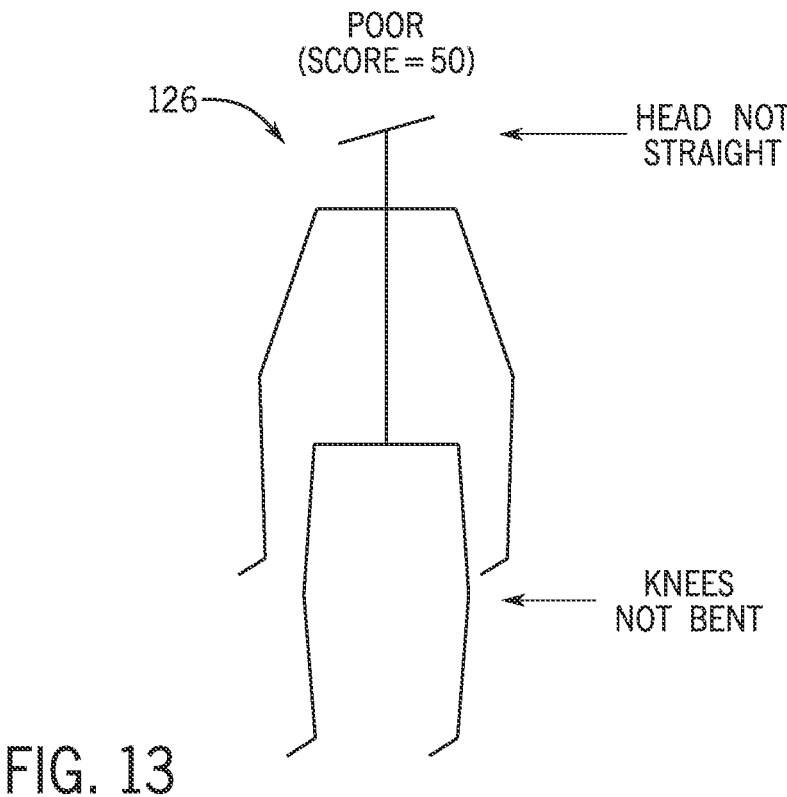
FIG. 13 illustrates recreated three-dimensional position and orientation data for various parts of the body of a worker performing a certain work function, in accordance with embodiments described herein.
Figure 14:
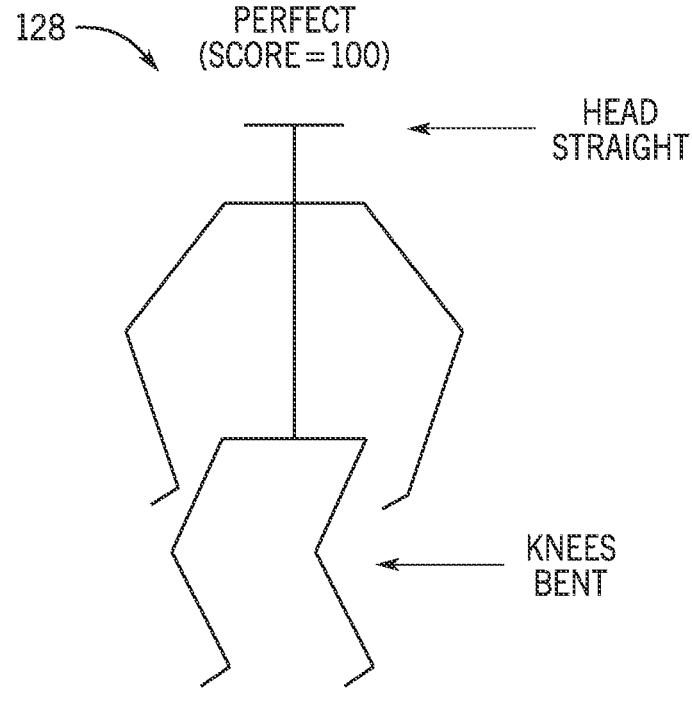
FIG. 14 illustrates three-dimensional position and orientation data for a known physical movement pattern relating to a particular work function, in accordance with embodiments described herein.

As an example, FIG. 13 illustrates recreated three-dimensional position and orientation data 126 for various parts of the body of a worker 12 performing a certain work function, and FIG. 14 illustrates three-dimensional position and orientation data 128 for a known physical movement pattern relating to a particular work function that has been determined by the work activity analysis system 18 and/or one or more user computing devices 32 to be analogous to the work function being performed by the worker 12 as illustrated in FIG. 13. For example, FIGS. 13 and 14 represent an actual worker 12 attempting to lift an object and an idealized worker 12 attempting to lift an object, respectively. Although illustrated in FIGS. 13 and 14 as only including a single snapshot in time of the recreated three-dimensional position and orientation data 126 and the three-dimensional position and orientation data 128 for a known physical movement pattern, it will be appreciated that the actual patterns of movement relating to the recreated three-dimensional position and orientation data 126 and the three-dimensional position and orientation data 128 for a known physical movement pattern may actually be correlated and compared over a given period of time that correlates to the time required to perform the work function being correlated in compared. As such, in certain embodiments, time offsets, time delays, and so forth, between the recreated three-dimensional position and orientation data 126 and the three-dimensional position and orientation data 128 for a known physical movement pattern may be taken into account by the work activity analysis system 18 and/or one or more user computing devices 32, for example, to allow for varying durations, pauses in activity, and so forth, of time to perform the work function being correlated in compared. Indeed, in certain embodiments, the work activity analysis system 18 and/or one or more user computing devices 32 may take such varying durations, pauses in activity, and so forth, into account when grading the actual work performance of the worker 12, as described in greater detail herein.

As illustrated in FIGS. 13 and 14, by recreating three-dimensional position and orientation data 126 for various parts of the body of an actual worker 12 performing a certain work function, and comparing the recreated three-dimensional position and orientation data 126 of the actual worker 12 performing the work function to three-dimensional position and orientation data 128 of an idealized worker 12 performing the analogous work function, the work activity analysis system 18 and/or one or more user computing devices 32 may determine a grade (e.g., using a tiered grading system, such as "Perfect", "Great", "Good", "Acceptable", "Poor", "and "Unacceptable", and so forth; using a number grading system, for example, on a scale of 0 to 100; and so forth) for the actual performance of the work function (e.g., FIG. 13) as compared to the idealized performance of the work function (e.g., FIG. 14), as well as identifying specific deficiencies (e.g., "Head Not Straight", "Knees Not Bent", and so forth) of the actual performance of the work function (e.g., FIG. 13) as compared to the idealized performance (e.g., "Head Straight", "Knees Bent", and so forth) of the work function (e.g., FIG. 14) and providing recommended modifications to the actual worker 12 for improvement of the work function (e.g., "Keep Your Head Straight", "Bend Your Knees", and so forth), for example, via the work activity analysis software 34 and/or the administrative work activity analysis software 48, as described in greater detail herein.

In addition, as described in greater detail herein, in certain embodiments, other types of tracked data (e.g., physiological data, temperature data, moisture data, pressure data, audio data, and so forth) may be used by the work activity analysis system 18 and/or one or more user computing devices 32 to determine if the actual worker 12 is struggling to perform the work function depicted by the recreated three-dimensional position and orientation data 126 of the actual worker 12 performing the work function. For example, in certain embodiments, the other types of tracked data may indicate that the heart rate of the worker 12 is higher than expected, that a skin temperature of the worker 12 is higher than expected, that the worker 12 is sweating more than expected, and so forth. In addition, in certain embodiments, all of the information illustrated in FIGS. 13 and 14 and described in reference to FIGS. 13 and 14, as well as additional information, may be provided via the work activity analysis software 34 and/or the administrative work activity analysis software 48 to aid the worker 12 in improving future performance of the work function and/or to aid a supervising worker 12 to aid the worker 12 in improving future performance of the work function.

In addition, as described in greater detail herein, in certain embodiments, additional physical activity data may be detected by one or more additional activity trackers 38 associated with the worker 12, and the additional physical activity data may be correlated with the physical activity data detected by the one or more sensors 16 of the work clothing 14 being worn by the worker 12 to, for example, find physical activity data that matches (e.g., suggesting a higher confidence in the matching physical activity data), find physical activity data that does not seem to match (e.g., suggesting a lower confidence in the non-matching physical activity data), and so forth. Similarly, in certain embodiments, the other types of tracked data (e.g., physiological data, temperature data, moisture data, pressure data, audio data, and so forth) may be correlated with similar data detected by one or more additional activity trackers 38 associated with the worker 12. In such embodiments, the work activity analysis system 18 and/or one or more user computing devices 32 may be configured to utilize data conversion protocols to correlate the data received from the one or more sensors 16 of the work clothing 14 being worn by the worker 12 and the data received from the one or more additional activity trackers 38 associated with the worker 12 such that the various data may be able to be compared with each other properly.

In addition to providing feedback (e.g., grading, identified deficiencies, recommended modifications, and so forth) relating to performance of certain work functions, in certain embodiments, the work activity analysis system 18 and/or one or more user computing devices 32 may be configured to provide additional beneficial information to the workers 12 (e.g., via the work activity analysis software 34 and/or the administrative work activity analysis software 48). For example, in certain embodiments, the work activity analysis software 34 and/or the administrative work activity analysis software 48 may provide indications to the workers 12 regarding health-related parameters for the workers 12, such as how long they are standing per day, an indication of blood flow in their limbs throughout the day, and so forth. In addition, in certain embodiments, the work activity analysis software 34 and/or the administrative work activity analysis software 48 may provide an indication of an amount of wear on certain items of work clothing 14, as well as when the workers 12 may want to replace certain items of work clothing 14 (e.g., as indicated by a predicted usable life span, as a function of total predicted wear versus actual wear). In addition, in certain embodiments, the work activity analysis software 34 and/or the administrative work activity analysis software 48 may provide recommendations relating to supplemental work clothing 14 (e.g., recommending inserts for certain types of work footwear 14A), warnings relating to potential health hazards (e.g., blisters), warnings relating to possible overexertion, and so forth.

FIG. 15 is a flow diagram of a method 130 of use of the work activity analysis and management system 10 of FIG. 1. As illustrated, in certain embodiments, the method 130 may include detecting, via one or more sensors 16 integrated into one or more work clothing items 14, physical activity data relating to one or more work functions performed by one or more workers 12 wearing the one or more work clothing items 14 (block 132). In addition, in certain embodiments, the method 130 may include analyzing, via one or more computing devices 18, 32, the physical activity data to determine one or more parameters relating to the one or more work functions performed by the one or more workers 12 (block 134). For example, in certain embodiments, the one or more parameters relating to the one or more work functions performed by the one or more workers 12 may include the determined grading, the identified deficiencies, the recommended modifications, and so forth, described above.

In addition, in certain embodiments, the method 130 may include causing, via one or more computing devices, the one or more parameters relating to the one or more work functions performed by the one or more workers 12 to be displayed via a display 36, 50 of the one or more computing devices 18, 32 (block 136). For example, in certain embodiments, the work activity analysis software 34 and the administrative work activity analysis software 48 being executed on the user computing devices 32 and the work activity analysis system 18, respectively, may be configured to display any and all of the parameters described herein relating to work activity via a respective display 36, 50.

In addition, in certain embodiments, the method 130 may include detecting, via one or more additional activity trackers 38 associated with the one or more workers 12, additional physical activity data relating to the one or more work functions performed by one or more workers 12 wearing the one or more work clothing items 14. In addition, in certain embodiments, the method 130 may include correlating, via the one or more computing devices 18, 32, the physical activity data with the additional physical activity data. In addition, in certain embodiments, the method 130 may include analyzing, via the one or more computing devices 18, 32, the physical activity data and the additional physical activity data to determine the one or more parameters relating to the one or more work functions performed by the one or more workers 12.

In addition, in certain embodiments, the method 130 may include determining, via the one or more computing devices 18, 32, one or more recommended modifications to performance of the one or more work functions based at least in part on the determined one or more parameters relating to the one or more work functions performed by the one or more workers 12. In addition, in certain embodiments, the method 130 may include causing, via the one or more computing devices 18, 32, the one or more recommended modifications to be displayed via the display 36, 50 of the one or more computing devices 18, 32.

While only certain features of the disclosure have been illustrated and described herein, many modifications and changes will occur to those skilled in the art. It is, therefore, to be understood that the appended claims are intended to cover all such modifications and changes as fall within the true spirit of the present disclosure.

The invention claimed is:

1. A method, comprising:

detecting, via one or more sensors integrated into one or more work clothing items, baseline positions and baseline orientations of the one or more work clothing items;

detecting, via the one or more sensors, physical activity data relating to one or more work functions performed by one or more workers wearing the one or more work clothing items, wherein the physical activity data comprises relative positions of the one or more work clothing items compared to the baseline positions, relative orientations of the one or more work clothing items compared to the baseline orientations, and/or relative movement of the one or more work clothing items;

determining, via one or more computing devices, idealized three-dimensional position and orientation data of an idealized worker performing known patterns of movement analogous to the one or more work functions performed by the one or more workers;

determining, via the one or more computing devices, a three-dimensional recreation of the one or more work functions performed by the one or more workers based on the detected physical activity data, wherein the detected physical activity data comprises actual patterns of movement relating to the three-dimensional recreation;

comparing, via the one or more computing devices, the three-dimensional recreation with the idealized three-dimensional position and orientation data over a period of time that correlates to a time required to perform the known patterns of movement, wherein comparing the three-dimensional recreation with the idealized three-dimensional position and orientation data comprises taking into account time offsets, time delays, or a combination thereof, when grading a work performance of the one or more workers;

analyzing, via the one or more computing devices, the three-dimensional recreation of the one or more work functions to determine one or more parameters relating to the one or more work functions performed by the one or more workers, wherein the one or more parameters relating to the one or more work functions comprise whether the one or more workers are performing the one or more work functions properly; and causing, via the one or more computing devices, the one or more parameters relating to the one or more work functions performed by the one or more workers to be displayed via a display of the one or more computing devices.

2. The method of claim 1, comprising:

detecting, via one or more additional activity trackers associated with the one or more workers, additional physical activity data relating to the one or more work functions performed by one or more workers wearing the one or more work clothing items, wherein the additional physical activity data comprises additional relative positions of the one or more work clothing items compared to the baseline positions, additional relative orientations of the one or more work clothing items compared to the baseline orientations, and/or additional relative movement of the one or more work clothing items;

determining, via the one or more computing devices, an additional three-dimensional recreation of the one or more work functions performed by the one or more workers based on the detected additional physical activity data;

correlating, via the one or more computing devices, the three-dimensional recreation of the one or more work functions and the additional three-dimensional recreation of the one or more work functions; and analyzing, via the one or more computing devices, the three-dimensional recreation of the one or more work functions and the additional three-dimensional recreation of the one or more work functions to determine the one or more parameters relating to the one or more work functions performed by the one or more workers.

3. The method of claim 1, comprising:

determining, via the one or more computing devices, one or more recommended modifications to performance of the one or more work functions based at least in part on the determined one or more parameters relating to the one or more work functions performed by the one or more workers; and causing, via the one or more computing devices, the one or more recommended modifications to be displayed via the display of the one or more computing devices.

4. The method of claim 1, comprising causing, via the one or more computing devices, one or more indications relating to health-related parameters for the one or more workers to be displayed via the display of the one or more computing devices.

5. The method of claim 1, comprising causing, via the one or more computing devices, an amount of wear on the one or more work clothing items to be displayed via the display of the one or more computing devices.

6. The method of claim 1, comprising causing, via the one or more computing devices, one or more recommendations relating to supplemental work clothing, one or more warnings relating to potential health hazards, one or more warnings relating to possible overexertion, or some combination thereof, to be displayed via the display of the one or more computing devices.

7. The method of claim 1, wherein the one or more work clothing items comprise one or more work boots, one or more work shoes, one or more work socks, one or more pairs of work pants, one or more work jackets, one or more work overalls, one or more work belts, one or more work goggles, one or more hard hats, one or more pairs of work gloves, or some combination thereof.

8. The method of claim 1, wherein grading the work performance comprises determining, via the one or more computing devices, a grade for the respective work performance of the one or more work functions as compared to the idealized three-dimensional position and orientation data of the idealized worker.

9. The method of claim 8, wherein the grade for the performance of the one or more work functions comprises a tiered grading system, a number grading system, or a combination thereof.

10. The method of claim 1, wherein the one or more parameters relating to the one or more work functions further comprise how long the one or more workers are standing per day, an indication of blood flow in one or more limbs of the one or more workers, or a combination thereof.

11. A work activity analysis system, comprising:

one or more processors configured to execute computer-executable instructions, wherein the instructions, when executed by the one or more processors, cause the one or more processors to:

receive baseline positions and baseline orientations of one or more work clothing items worn by one or more workers;

receive physical activity data relating to one or more work functions performed by the one or more workers from the one or more work clothing items worn by the one or more workers, wherein the physical activity data comprises relative positions of the one or more work clothing items compared to the baseline positions, relative orientations of the one or more work clothing items compared to the baseline orientations, and/or relative movement of the one or more work clothing items;

determine idealized three-dimensional position and orientation data of an idealized worker performing known patterns of movement analogous to the one or more work functions performed by the one or more workers;

determine a three-dimensional recreation of the one or more work functions performed by the one or more workers based on the received physical activity data, wherein the received physical activity data comprises actual patterns of movement relating to the three-dimensional recreation;

compare the three-dimensional recreation with the idealized three-dimensional position and orientation data over a period of time that correlates to a time required to perform the known patterns of movement, wherein comparing the three-dimensional recreation with the idealized three-dimensional position and orientation data comprises taking into account time offsets, time delays, or a combination thereof, when grading a respective work performance of the one or more workers;

analyze the three-dimensional recreation of the one or more work functions to determine one or more parameters relating to the one or more work functions performed by the one or more workers, wherein the one or more parameters relating to the one or more work functions comprise whether the one or more workers are performing the one or more work functions properly;

provide one or more recommended modifications for improving the respective work performance of the one or more workers based on the one or more parameters and the analyzed three-dimensional recreation;

provide one or more recommendations relating to supplemental work clothing based on the one or more parameters and the analyzed three-dimensional recreation; and display the one or more parameters relating to the one or more work functions performed by the one or more workers via a display of the work activity analysis system.

12. The work activity analysis system of claim 11, wherein the instructions, when executed by the one or more processors, cause the one or more processors to cause the one or more recommended modifications to be displayed via the display of the work activity analysis system.

13. The work activity analysis system of claim 11, wherein the instructions, when executed by the one or more processors, cause the one or more processors to determine a grade for the respective work performance of the one or more work functions as compared to the idealized three-dimensional position and orientation data of the idealized worker.

14. The work activity analysis system of claim 13, wherein the grade for the performance of the one or more work functions comprises a tiered grading system, a number grading system, or a combination thereof.

15. The work activity analysis system of claim 11, wherein the one or more parameters relating to the one or more work functions further comprise how long the one or more workers are standing per day, an indication of blood flow in one or more limbs of the one or more workers, or a combination thereof.

* * * * *